US008649478B2

(12) United States Patent
Kobayashi

(10) Patent No.: US 8,649,478 B2
(45) Date of Patent: Feb. 11, 2014

(54) X-RAY CT SCANNER AND CONTROL PROGRAM THEREOF

(75) Inventor: Masaki Kobayashi, Oume (JP)

(73) Assignee: Hitachi Aloka Medical, Ltd., Mituka-shi, Tokyo (JP)

( * ) Notice: Subject to any disclaimer, the term of this patent is extended or adjusted under 35 U.S.C. 154(b) by 172 days.

(21) Appl. No.: 12/671,776

(22) PCT Filed: Jan. 14, 2009

(86) PCT No.: PCT/JP2009/050790
§ 371 (c)(1),
(2), (4) Date: Feb. 2, 2010

(87) PCT Pub. No.: WO2009/110252
PCT Pub. Date: Sep. 11, 2009

(65) Prior Publication Data
US 2011/0228897 A1 Sep. 22, 2011

(30) Foreign Application Priority Data
Mar. 7, 2008 (JP) ................................. 2008-057478

(51) Int. Cl.
*A61B 6/00* (2006.01)
(52) U.S. Cl.
USPC .................................................. 378/8; 378/4
(58) Field of Classification Search
USPC .......................................................... 378/4, 8
See application file for complete search history.

(56) References Cited

U.S. PATENT DOCUMENTS

| 4,417,353 | A | * | 11/1983 | Groh et al. | ......................... 378/4 |
| 5,751,782 | A | | 5/1998 | Yoshitome | |
| 5,832,051 | A | * | 11/1998 | Lutz | ................................. 378/8 |
| 6,233,478 | B1 | * | 5/2001 | Liu | .............................. 600/428 |

(Continued)

FOREIGN PATENT DOCUMENTS

| JP | 9-024045 A | 1/1997 |
| JP | 2000-139892 A | 5/2000 |

(Continued)

OTHER PUBLICATIONS

Notification of Transmittal of Translation of the International Preliminary Report on Patentability (Form PCT/IB/338) of International Application No. PCT/JP2009/050790 mailed Oct. 21, 2010 with Forms PCT/IB/326, PCT/IB/373 and PCT/ISA/237.

(Continued)

*Primary Examiner* — Alexander H Taningco
(74) *Attorney, Agent, or Firm* — Westerman, Hattori, Daniels & Adrian, LLP

(57) ABSTRACT

An X-ray CT scanner performs CT imaging twice on a single imaging site such that respiratory phases relative to rotation of a measuring unit (X-ray generator and X-ray detector) are inverted with respect to each other. For determining a start time of the second CT imaging, a respiration cycle and the like are calculated according to projection data acquired by the first CT imaging. Further, sinograms 70a and 70b are generated, on each of which sets of projection data acquired from each CT imaging are arranged in the order of rotational angles. Subsequently, a corrected sinogram is generated in which sets of data fluctuated portions b and f attributable to respiration in the first sinogram 70a are replaced with data of the corresponding portions in the second sinogram 70b. Finally, a tomographic image is generated on the basis of the corrected sinogram.

8 Claims, 13 Drawing Sheets

(56) References Cited

U.S. PATENT DOCUMENTS

| | | | |
|---|---|---|---|
| 6,236,705 B1* | 5/2001 | Stergiopoulos et al. | 378/8 |
| 6,256,368 B1* | 7/2001 | Hsieh et al. | 378/8 |
| 6,353,653 B1* | 3/2002 | Edic | 378/8 |
| 6,421,552 B1* | 7/2002 | Hsieh | 600/425 |
| 6,434,215 B1* | 8/2002 | Cesmeli | 378/8 |
| 6,435,714 B1* | 8/2002 | Bruder | 378/196 |
| 6,504,893 B1* | 1/2003 | Flohr et al. | 378/8 |
| 6,522,712 B1* | 2/2003 | Yavuz et al. | 378/4 |
| 6,639,965 B1* | 10/2003 | Hsieh et al. | 378/8 |
| 6,909,769 B2* | 6/2005 | Bruder et al. | 378/8 |
| 7,020,234 B2* | 3/2006 | Bruder et al. | 378/8 |
| 7,039,152 B2* | 5/2006 | Bruder et al. | 378/8 |
| 7,042,975 B2* | 5/2006 | Heuscher | 378 |
| 7,313,215 B2* | 12/2007 | Hsieh et al. | 378/15 |
| 7,570,733 B2* | 8/2009 | Hsieh et al. | 378/8 |
| 2002/0025017 A1* | 2/2002 | Stergiopoulos et al. | 378/8 |
| 2002/0136350 A1* | 9/2002 | Pan et al. | 378/8 |
| 2004/0136490 A1 | 7/2004 | Edic et al. | |
| 2005/0201509 A1* | 9/2005 | Mostafavi et al. | 378/8 |
| 2006/0056578 A1 | 3/2006 | Rubin et al. | |
| 2006/0178575 A1* | 8/2006 | Piacsek et al. | 600/413 |
| 2006/0210016 A1* | 9/2006 | Francke | 378/22 |
| 2006/0285632 A1 | 12/2006 | Boese et al. | |
| 2007/0030946 A1* | 2/2007 | Tsuyuki et al. | 378/8 |
| 2007/0104309 A1* | 5/2007 | Schonborn et al. | 378/4 |
| 2007/0197907 A1 | 8/2007 | Bruder et al. | |

FOREIGN PATENT DOCUMENTS

| | | |
|---|---|---|
| JP | 2006-239049 A | 9/2006 |
| JP | 2006-311941 A | 11/2006 |
| JP | 2007-167656 A | 7/2007 |
| WO | 99/07283 A1 | 2/1999 |
| WO | 2006/029336 A2 | 3/2006 |

OTHER PUBLICATIONS

Supplementary European Search Report dated May 6, 2011, issued in corresponding European Patent Application No. 09717809.9.
International Search Report of PCT/JP2009/050790, mailing date of Apr. 7, 2009.

* cited by examiner

X-RAY CT SCANNER AND CONTROL PROGRAM THEREOF

TECHNICAL FIELD

The present invention relates to X-ray CT scanners for generating a tomographic image of a subject based on projection data obtained by irradiating the subject with X-rays.

BACKGROUND ART

Known X-ray CT scanners typically include an X-ray generator and an X-ray detector arranged opposite each other across a subject, and CT imaging is performed through irradiation and detection of X-rays while the X-ray generator and the X-ray detector are rotated relative to the subject. In the process of CT imaging, projection data indicating the degree of X-ray attenuation (degree of X-ray absorption by the subject) is collected at each rotational angle, and a tomographic image (CT image) of the subject is generated based on the obtained projection data.

During the process of CT imaging, if an imaging target site such as an organ moves due to body motion of the subject including respiratory motion, artifacts are generated in the final CT image. As such, respiratory synchronized scanning, in which respiratory motion of a subject is detected and CT imaging (scanning) is performed in synchronization with a phase where motion of the organ due to respiration is determined to be least likely, has been proposed in, for example, Japanese patent publications JP 2000-139892 A and JP 2006-311941 A (Patent Documents 1 and 2 listed below). By employing such an art, generation of artifacts due to body motion can be reduced, thereby enabling capturing of higher quality CT images.

PRIOR ART DOCUMENTS

Patent Documents

PATENT DOCUMENT 1: JP 2000-139892 A
PATENT DOCUMENT 2: JP 2006-311941 A

SUMMARY OF THE INVENTION

Problems to be Solved by the Invention

However, the above-described art employs a dedicated detection device, such as, for example, a respiration detector, for detecting body motion, causing problems such as increased cost of the overall diagnosis system including an X-ray CT scanner and a complicated configuration for the system. Further, as a respiration detector of this kind must be appropriately attached to and detached from a subject, significant time and effort are needed. Also, there are often instances where a respiration detector attached to a subject appears in a captured CT image, thereby degrading the quality and impairing the reliability of the CT image. As such, acquiring a preferable CT image in which influences of body motion are reduced remains problematic today.

In view of the above problems with the conventional art, the present invention provides an X-ray CT scanner capable of generating preferable CT images, and its control program.

Means for Solving the Problems

An X-ray CT scanner of the present invention includes a measurement section that performs CT imaging by irradiating an X-ray while relatively rotating an X-ray generator and an X-ray detector, arranged opposite each other across a subject, with respect to the subject, and collecting detection result data detected by the X-ray detector at each prescribed rotational angle; a body motion characteristic calculation section that extracts a data fluctuation caused by body motion of the subject from the detection result data obtained by the CT imaging, and calculates characteristics of the body motion of the subject based on the extracted result; a drive control section that allows the measurement section to perform CT imaging on the same target site a plurality of times, the drive control section controlling execution of the second CT imaging or after based on the body motion characteristics calculated by the body motion characteristic calculation section such that phases of the body motion relative to rotational angles of the X-ray generator and the X-ray detector differ between the plurality of times of CT imaging; and an image generation section that generates a tomographic image in which an influence of the body motion is eliminated or reduced, based on projection data obtained by performing CT imaging a plurality of times.

In a preferable aspect, the image generation section includes a sinogram generation section that generates a sinogram by arranging pieces of projection data obtained by the CT imaging in the order of the rotational angles; a sinogram correction section that generates a corrected sinogram in which the data fluctuation caused by the body motion is reduced or eliminated, from a plurality of sinograms corresponding to the same imaging site; and a tomographic image generation section that generates a tomographic image based on the corrected sinogram.

In another preferable aspect, the body motion characteristic calculation section extracts the data fluctuations caused by the body motion after eliminating or reducing data fluctuations caused by rotation of the X-ray generator and the X-ray detector from the detection result data obtained by the CT imaging.

In another preferable aspect, when the $(N+1)^{th}$ CT imaging is performed on the same imaging site, the body motion characteristic calculation section calculates body motion characteristics based on detection result data obtained by the $N^{th}$ CT imaging, and the drive control section determines a start time of the $(N+1)^{th}$ CT imaging based on the body motion characteristics calculated from the detection result data of the $N^{th}$ CT imaging. Further, it is also desirable that the body motion characteristic calculation section recalculates body motion characteristics each time the imaging target site is changed.

In another preferable aspect, the sinogram correction section compensates a data fluctuated portion caused by body motion in one sinogram with data of a corresponding angular portion in another sinogram of the same imaging target site. In that case, for an angular portion where no data fluctuation is caused by body motion in all of the plurality of sinograms of the same imaging target site, the sinogram correction section calculates an average between the plurality of sinograms.

A control program for an X-ray CT scanner, according to another aspect of the present invention allows a computer which is connected to a measurement device that performs CT imaging by irradiating an X-ray while relatively rotating an X-ray generator and an X-ray detector, arranged opposite each other across a subject, with respect to the subject and collecting detection result data detected by the X-ray detector at each prescribed rotational angle, to function as: a body motion characteristic calculation section that extracts a data fluctuation caused by body motion of the subject from the detection result data obtained by the CT imaging, and calculates characteristics of the body motion of the subject based on the extracted result; a drive control section that allows the measurement section to perform CT imaging on the same target site a plurality of times, the drive control section controlling execution of the second CT imaging or after based on the body motion characteristic calculated by the body motion characteristic calculation section such that phases of the body motion relative to rotational angles of the X-ray generator and the X-ray detector differ between the plurality of times of CT imaging; and an image generation section that generates a tomographic image in which an influence of the body motion is eliminated or reduced, based on projection data obtained by the CT imaging performed a plurality of times.

Advantages of the Invention

According to the present invention, body motion characteristics are calculated from detection result data obtained through CT imaging, and, by using the calculated body motion characteristics, a corrected sinogram in which data fluctuations caused by body motion are reduced or eliminated is obtained. CT images of higher quality and greater reliability can be acquired using the corrected sinogram in which data fluctuations caused by body motion are reduced or eliminated.

DESCRIPTION OF EMBODIMENT

Figure 1:
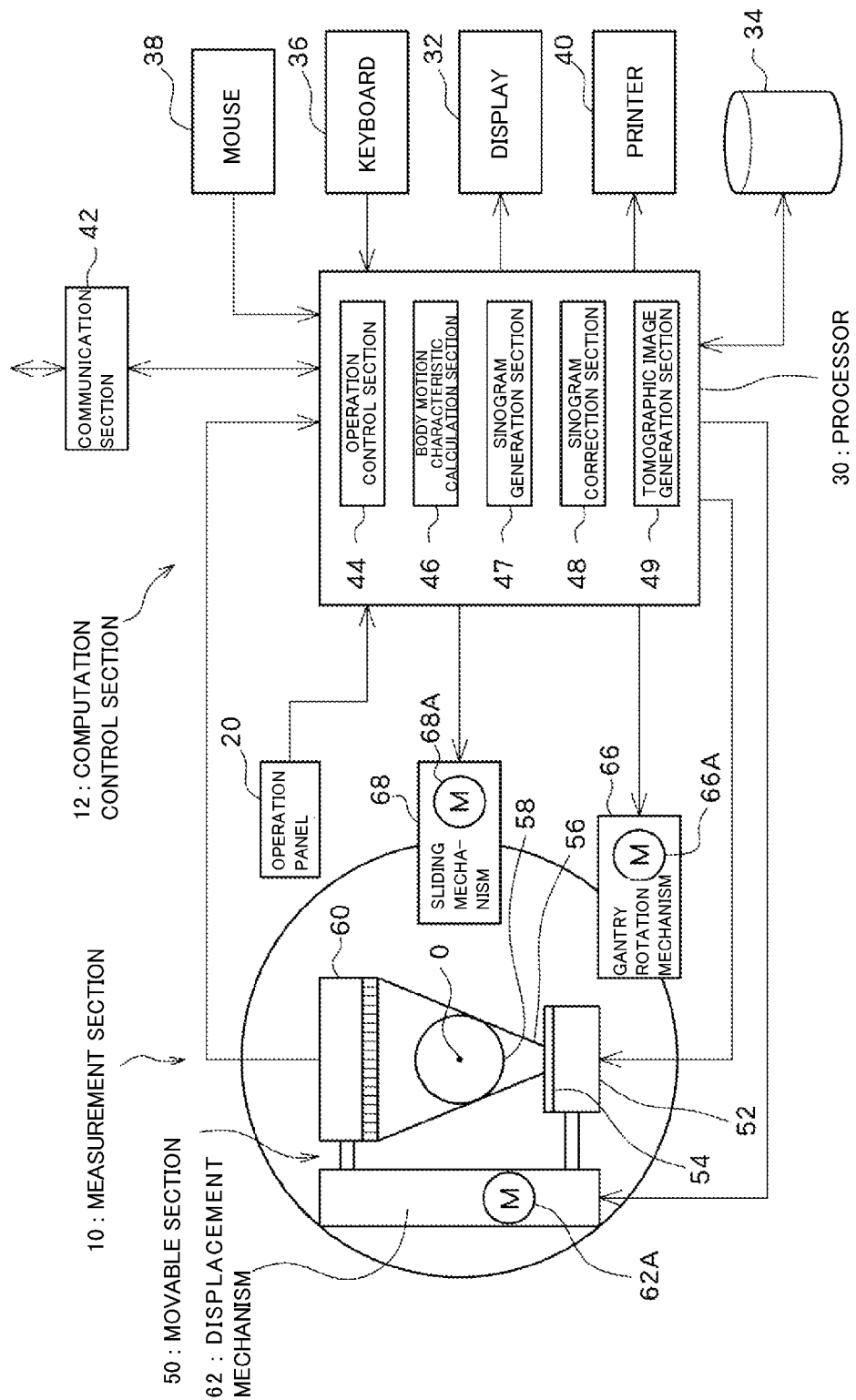
FIG. 1 is a block diagram showing the configuration of an X-ray CT scanner according to an embodiment of the present invention.
Figure 2:
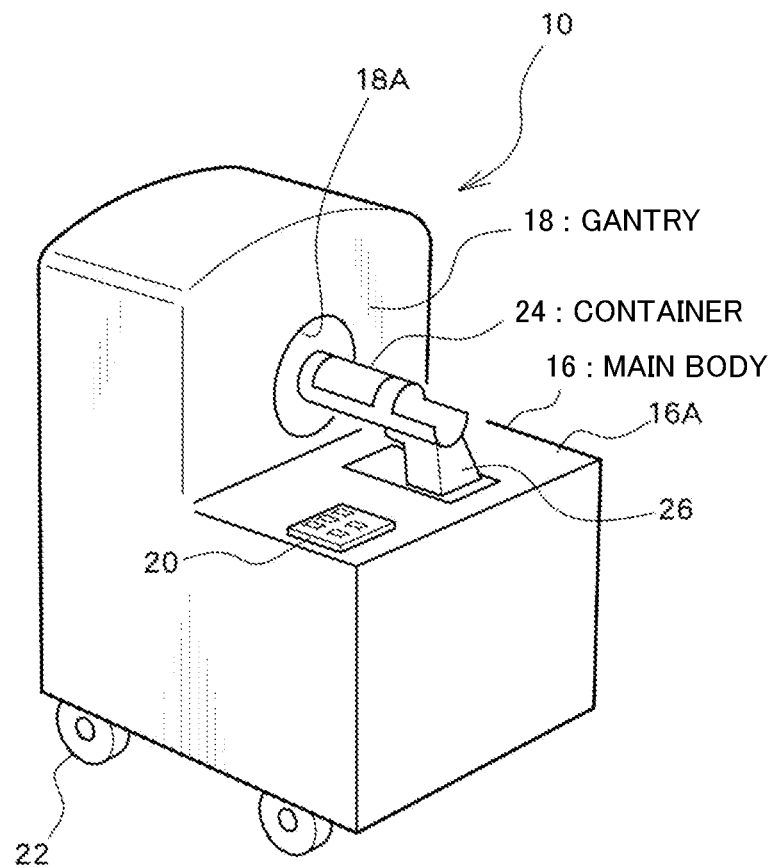
FIG. 2 is a perspective view of a measurement section.

Hereinafter, an embodiment of the present invention will be described with reference to the drawings. FIG. 1 is a block diagram showing the configuration of an X-ray CT scanner according to this embodiment of the present invention. FIG. 2 is a perspective view of a measurement section 10 of the X-ray CT scanner.

As is well known, an X-ray CT scanner is an apparatus for generating tomographic images (CT images) of a subject based on projection data obtained by irradiating the subject with X-rays.

The X-ray CT scanner of the present embodiment has, in addition to a tomographic image generating function, a function of detecting characteristics of body motion of a subject, such as a cycle of body motion. By using the detected body motion characteristics, the scanner according to the present embodiment makes it possible to generate more preferable tomographic images. This X-ray CT scanner will be described below in detail.

The example X-ray CT scanner described in the present embodiment is adapted for preferable use where subjects are small animals, such as mice, rats, guinea pigs, and hamsters. However, by changing the configurations of a gantry 18 and a container 24 described below, the scanner can also be used for imaging of human beings.

As shown in FIG. 1, the components of the X-ray CT scanner are broadly divided into a measurement section 10 for obtaining projection data, and a computation control unit 12 for controlling drive of the measurement section 10 and performing various computations based on the obtained projection data.

As shown in FIG. 2, the measurement section 10 has a main body with a gantry 18. An opening is formed in an upper surface 16A of the main body 16, and an arm 26 protrudes upward from the opening. The arm 26 constitutes a part of a sliding mechanism 26, and is linked to the container 24 so as to allow slidable movement (moving scanning) of the container 24 in a direction of the rotational center axis.

On the other hand, the gantry 18 accommodates a measurement unit configured of an X-ray generator 52 and an X-ray detector 60. This measurement unit rotationally moves around the rotational center axis. In the center part of the gantry 18, a cavity 18A is formed in a direction of the rotational center axis. Although the cavity 18A in this example is not a through-hole, the cavity 18A may be configured as a through-hole.

A container 24 is a capsule for holding a subject, such as, for example, a small animal or an organ extracted therefrom, having, in this embodiment, a hollow, almost cylindrical shape. The container 24 is arranged such that the center axis of the container coincides with the rotational center axis. Specifically, the base end portion of the container 24 is mounted on the top end portion of the arm 26 in a detachable manner. Attachment mechanisms may be various engaging mechanisms or threading mechanisms. As described above, the container 24 has a hollow cylindrical shape, and, in the present example, one or a plurality of small animals are arranged therein. With this configuration, it is possible to prevent the fur of small animals from directly contacting the gantry 18. Further, it is also possible to prevent bodily waste or shed hairs from being discharged to the outside. Furthermore, because it is possible to constrain small animals in the container 24 with a restraining device, problems such as image blurring caused when the CT image is reconstructed can be prevented. It should be noted that it is desirable to prepare various type of containers having different sizes and shapes for selective use.

After the container 24 is mounted on the arm 26, the arm 26 is driven forward along the direction of the rotational center axis. Thereby, the container 24 is installed in the cavity 18A of the gantry 18. At this stage, the container 24 is positioned such that an X-ray beam is projected onto the measurement position of the subject, and such measurement position is changed continuously or in stages. As a result, a plurality of CT cross-sections spatially aligned at predetermined pitches are formed.

The upper surface 16A of the main body 16 has an operation panel 20 thereon, the operation panel 20 including a plurality of switches and indicators. With the operation panel 20, a user can control operation of the devices at the measuring location. The main body 16 has a plurality of casters 22 in the lower part thereof.

In the measurement section 10, the X-ray generator 52 is provided on one side and the X-ray detector 60 is provided on the other side across the rotational center axis 0 (see FIG. 1). On the irradiating side of the X-ray generator 52, a collimator 54 is provided. The X-ray generator 52 irradiates an X-ray beam 56 of the intensity corresponding to the driving voltage supplied. This X-ray beam is in divergent or fan-like shape (namely, a fan beam shape) as shown in FIG. 1. On the other hand, the X-ray detector 60 is formed such that a plurality of (e.g., 100) X-ray detecting elements are arranged in a line, and an X-ray receiving opening is set in accordance with the opening angle of the X-ray beam 56. It should be noted that the arrangement of the X-ray detecting elements may be in a straight line or a circular arc. In the present embodiment, high-sensitivity X-ray detecting elements are used. Values detected by the X-ray detector 60 are output to the processor 30 as projection data. It should be noted that a voltage source connected to the X-ray generator 52, a signal processing circuit connected to the X-ray detector 60 and the like are not shown in FIG. 1.

In FIG. 1, area 58 indicates an effective field of view. This is a circular region where a CT image can be formed when the X-ray beam 56 is rotationally scanned. This effective field of view is determined in part by the positional relationship between the rotational center axis, X-ray generator 52, and the X-ray detector 60. As a displacement mechanism is provided in the present embodiment, it is possible to mechanically vary the magnification of a CT image by changing this positional relationship.

Here, the displacement mechanism 62 is linked to the X-ray generator 52 and the X-ray detector 60, and displaces these components, which comprise the measurement unit, in a beam axis direction of the X-ray beam 56 while maintaining the distance between them. Because the rotational center axis 0 remains unchanged, the magnification can be changed by moving the measurement unit without moving the container. It should be noted that the displacement mechanism 62 includes a motor 62A for generating a displacement force.

The gantry rotating mechanism 66 is a mechanism which rotates a rotating base to thereby rotationally drive all components, including the displacement mechanism, mounted on the rotating base. As the displacement mechanism 62 is provided with a measurement unit, the measurement unit positioned at a desired position by the displacement mechanism 62 is rotationally driven while the position thereof is maintained. The gantry rotating mechanism 66 has a motor 66A for generating its driving force.

The sliding mechanism 68 is a moving mechanism for allowing sliding movement of the arm shown in FIG. 2, and its driving force is generated by a motor 68A. The operation panel 20 is provided to the upper surface of the main body as described above. It is also acceptable that the operation panel 20 is connected to a local controller (not shown) provided to the measuring section 10 side such that the local controller and the computation control section 12 communicate with each other.

It is preferable to provide sensors for detecting the positions or positional changes provided by the various mechanisms 62, 66, 68 and the like shown in FIG. 1. It is also preferable that the computation control section 12 performs feedback control based on output signals of those sensors. Further, changes of magnifications provided by the displacement mechanism 62 may be performed by a user input or performed such that the size of a subject or the size of a container is automatically detected and a magnification is automatically set based on the detected data. Further, when information such as the type and the like of a container have been registered beforehand, a magnification may be set based on the registered information. Further, although in the example shown in FIG. 1 a motor 68A is provided to drive the sliding mechanism 68, the sliding force may be provided by human effort.

Next, the computation control section 12 will be described. A processor 30 is connected with a display 32, a storage device 34, a keyboard 36, a mouse 38, a printer 40, and the like, and also connected with a communication section 42 for performing communications with external devices over networks.

The processor 30 is configured by a CPU which executes various programs. FIG. 1 shows the main functions thereof. The processor 30 functions as an operation control section 44, a body motion characteristic calculation section 46, a sinogram generation section 47, a sinogram correction section 48, a tomographic image generation section 49, and the like.

The operation control section 44 controls driving of the measurement section 10. More specifically, the operation control section 44 controls driving of the gantry rotating mechanism 66, the X-ray generator 52, the X-ray detector 60 and the like to perform CT imaging. CT imaging is imaging performed for generating a tomographic image, and comprises operations of irradiating and detecting an X-ray while rotating the X-ray generator 52 and the X-ray detector 60 relative to a subject. Although CT imaging has conventionally normally been performed once on each site, in the present embodiment, CT imaging is performed a plurality of times on one imaging site, as described in detail below. Projection data obtained as a result of CT imaging is output to the body motion characteristic calculation section 46 and the sinogram generation section 47.

The body motion characteristic calculation section 46 calculates characteristics of body motion of a subject based on projection data obtained by CT imaging. As used here, body motion refers to periodic motion performed by a subject, such as respiratory and heartbeat motion, for example. Examples of characteristics of body motion include a periodic cycle of body motion and a continuing time that an imaging target is displaced (displacement time) due to respiratory motion. Calculation of body motion characteristics by the body motion characteristic calculation section 46 is normally performed each time CT imaging is performed. The body motion characteristics, calculated for each CT imaging, are used for controlling a start time of the next CT imaging and the like. If there is no next CT imaging, or if the imaging site is changed in the next CT imaging, calculation of body motion characteristics becomes unnecessary. This means that if CT imaging is performed N times on one imaging site, calculation of body motion characteristics is unnecessary in the $N^{th}$ time.

The sinogram generation section 47, as can be understood from its name, is a component section which generates sinograms. A sinogram shows sets of projection data obtained by CT imaging arranged in the order of rotational angles. This will be described with reference to FIG. 3.

Figure 3:
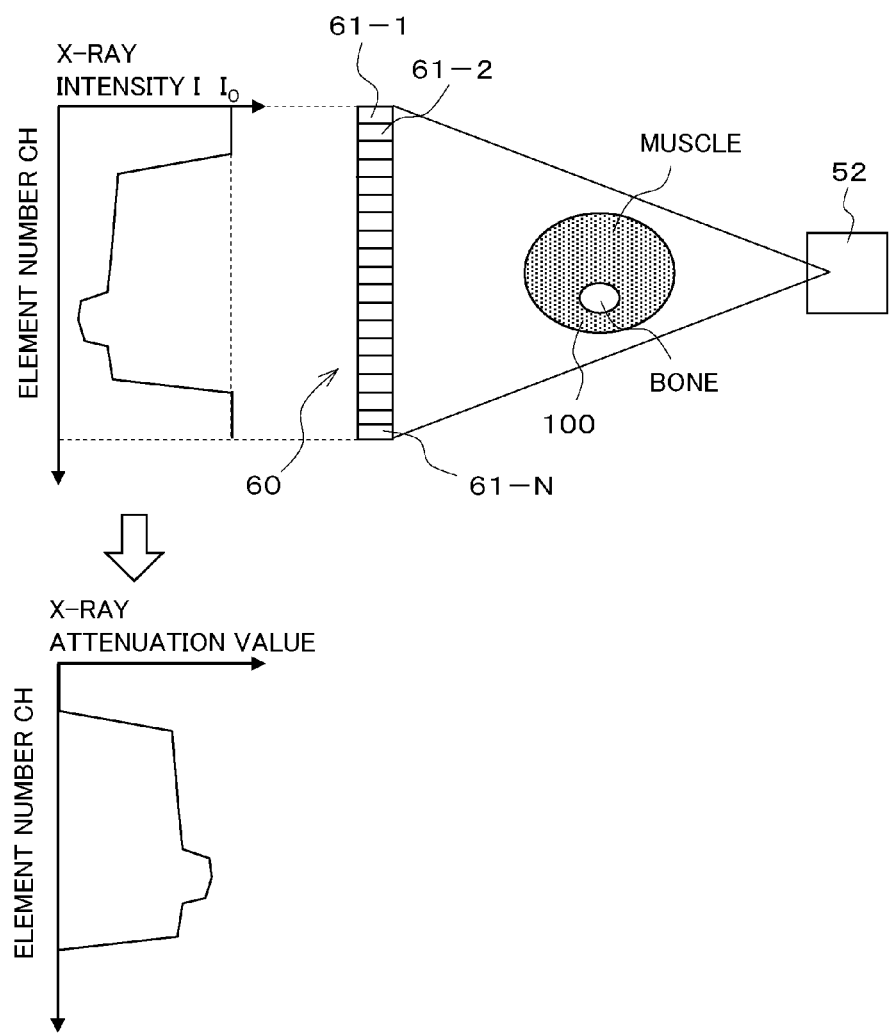
FIG. 3 is an illustration showing the principle of CT imaging.

FIG. 3 illustrates the basic principle of CT imaging. As described above, in the measurement section 10, the X-ray generator 52 and the X-ray detector 60 are arranged opposite each other across a subject 100. A portion of X-rays emitted from the X-ray generator 52 are absorbed by the subject 100, while a portion reach the X-ray detector 60. Detection elements 61_1, 61_2, ..., and 61_N provided to the X-ray detector 60 detect the intensity I of the incident X-rays. Data obtained by converting the detected X-ray intensity I into an X-ray attenuation value R is projection data, wherein the X-ray attenuation value $R = \log_e (I_0/I)$.

Figure 4:
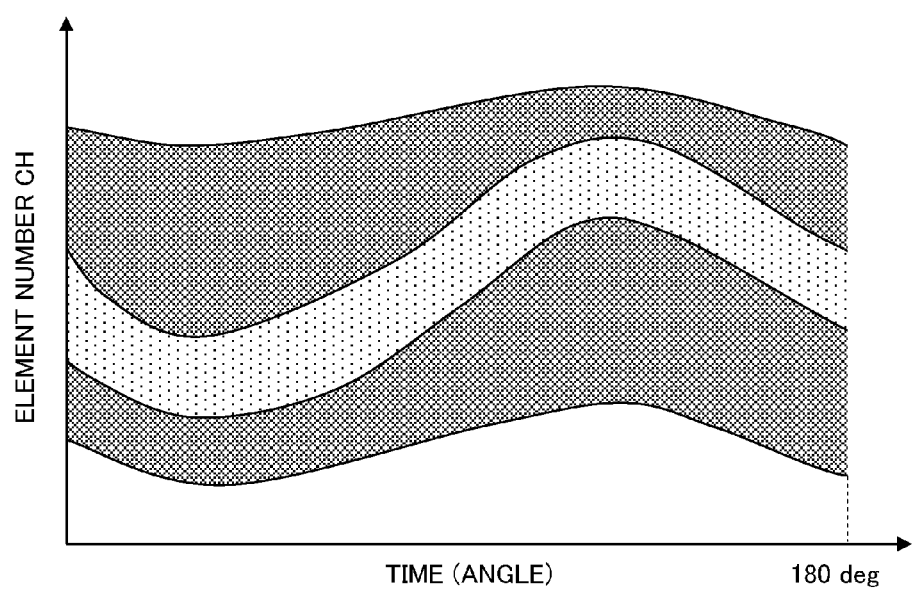
FIG. 4 shows an exemplary image of a sinogram.

In the present embodiment, the X-ray generator 52 and the X-ray detector 60 are rotated 180 degrees relative to the subject 100 in one CT imaging. When being rotated, projection data is output at each prescribed rotational angle. Projection data obtained at respective prescribed rotational angles are displayed as a sinogram, in which the data are arranged with the horizontal axis being the rotational angle and the vertical axis being the element number. FIG. 4 shows a sinogram in which the X-ray attenuation value R is imaged as a luminance value.

As noted above, in the present embodiment CT imaging is performed a plurality of times for each imaging site, and the sinogram generation section 47 generates a sinogram each time CT imaging is performed. As such, for one imaging site a plurality of sinograms are generated and output to the sinogram correction section 48.

The sinogram correction section 48 is a section for correcting calculated sinograms to eliminate or reduce influence of body motion. A sinogram which has been corrected is output to the tomographic image generation section 49 as a corrected sinogram.

In the tomographic image generation section 49, a tomographic image is generated based on the corrected sinogram. As well-known conventional art can be used to generate a tomographic image based on a sinogram, the detailed description thereof is omitted. The obtained tomographic image is shown on the display 32. A user makes a diagnosis or the like of the internal state of the subject based on the tomographic image shown on the display 32.

Next, operation of the X-ray CT scanner will be described in detail. As described above, the X-ray CT scanner of the present embodiment calculates motion characteristics based on the projection data obtained as a result of CT imaging, for the reasons explained below using respiratory motion as an example.

Figure 5:
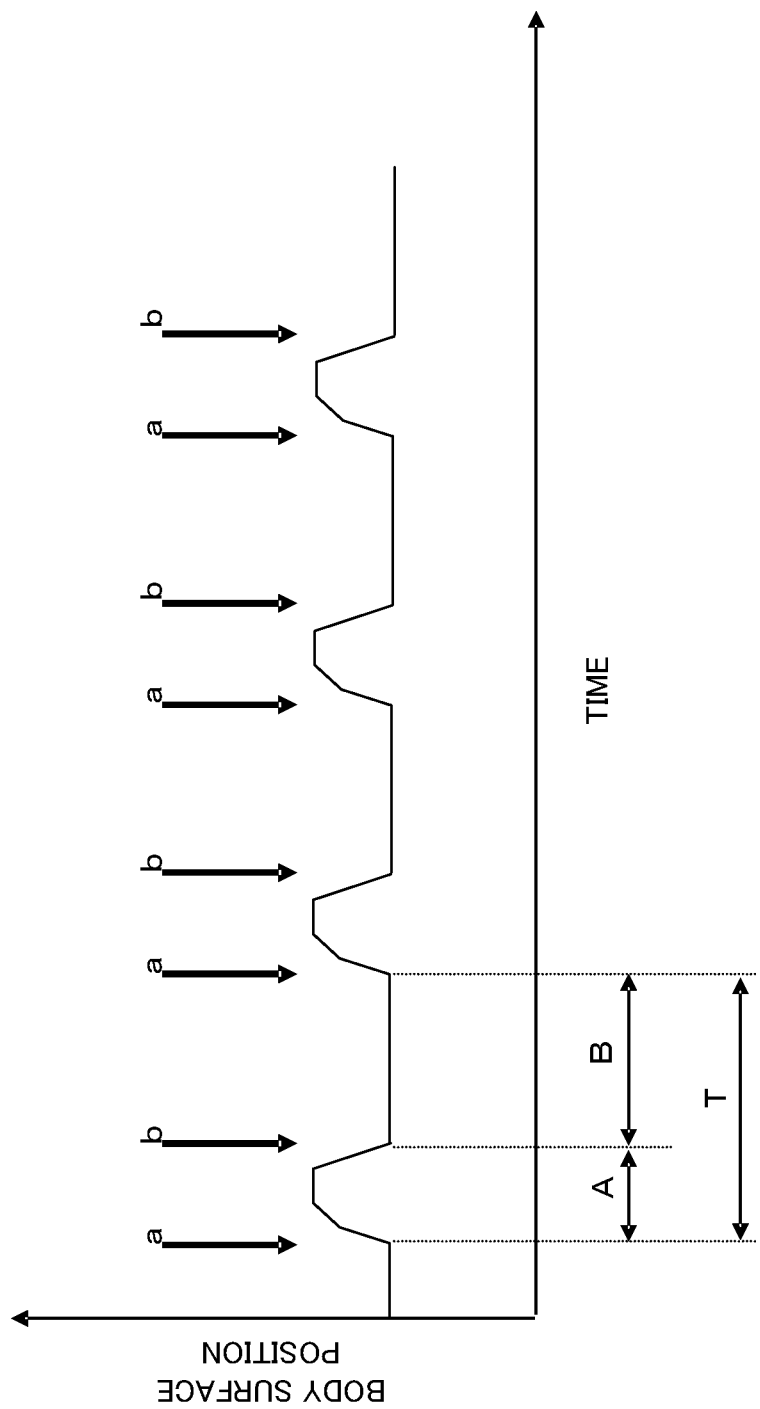
FIG. 5 is a graph showing body surface motion of a subject's chest due to respiration.

FIG. 5 is a graph schematically showing positional displacement of the body surface in the chest area of a rat sleeping under anesthesia. In FIG. 5, arrows "a" indicate start times of respiratory motion associated with inhalation, and arrow s "b" indicate start times of respiratory motion for exhaling. As is obvious from FIG. 5, the rat's chest is almost at rest after exhalation, but moves during inhalation. In the following description, the period B from the time "b" to the time "a", during which the chest is nearly at rest, is referred to as a "rest period", while the period A from the time "a" to the time "b", during which the chest is moving, is referred to as a "period of motion". The movement of the subject in the period of motion naturally affects the detected projection data. Specifically, the X-ray attenuation value detected during the period of motion A tends to be less than the X-ray attenuation value detected during a rest period.

Figure 13:
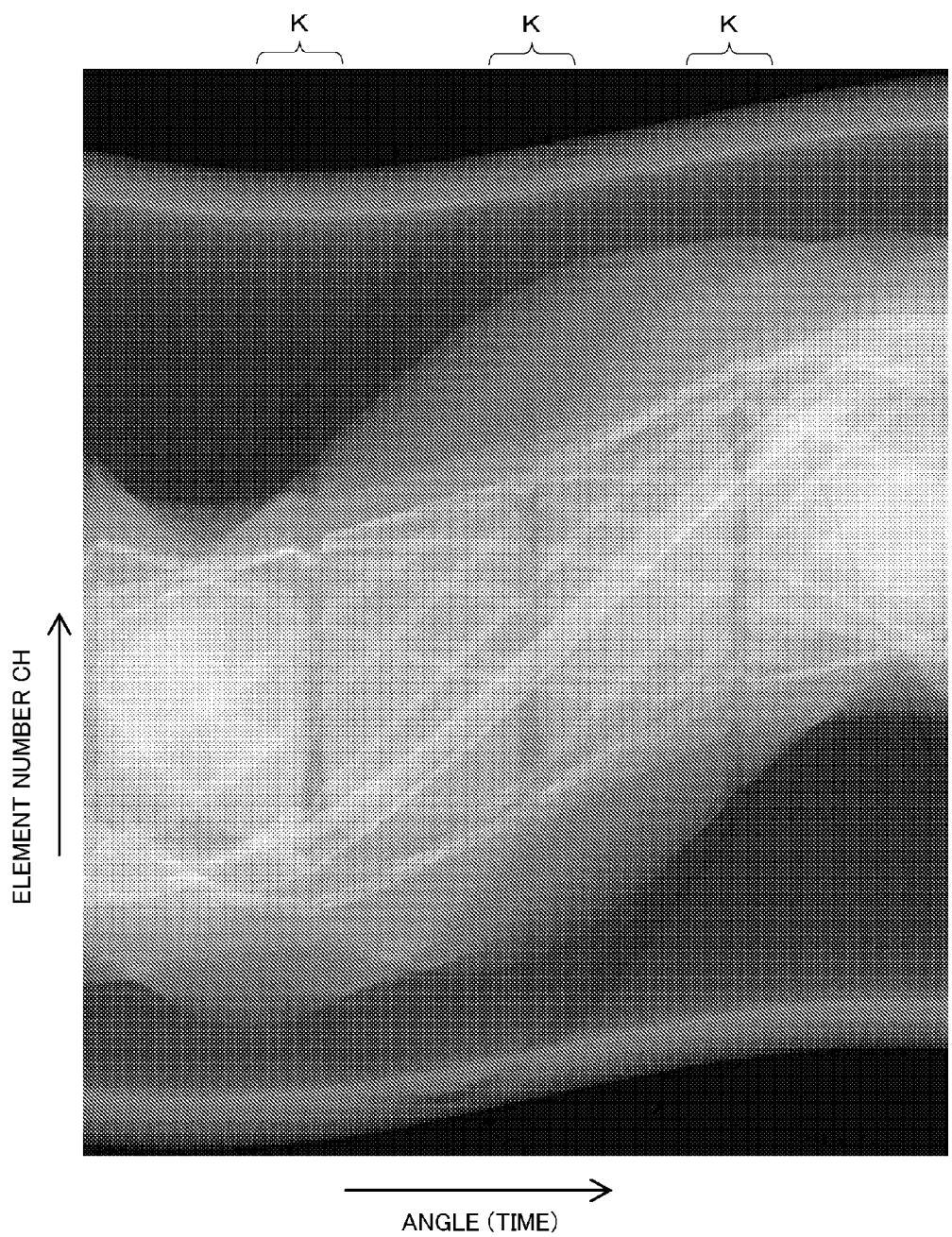
FIG. 13 shows an example of a sinogram.

FIG. 13 is a sinogram generated based on projection data obtained by CT imaging performed during respiratory motion. From FIG. 13, it can be that a portion K where the X-ray attenuation value is reduced (luminance is lowered) appears periodically. The portion K where the X-ray attenuation value is reduced corresponds to the period of motion A. If a tomographic image is generated based on projection data in which influences of the motion of the subject in the period of motion A remain, a virtual image called a motion artifact is generated in the tomographic image.

Techniques to detect respiration of a subject and perform CT imaging in synchronization with body motion by using the detected result have been known conventionally. However, in such a conventional technique, a dedicated respiratory sensor is used for detecting respiratory motion. Use of a respiratory sensor causes not only a problem of a cost increase, but also a problem that extra care is required in order to attach and detach the respiratory sensor to and from the subject. Further, there are also cases wherein a respirator sensor attached to the subject appears in a tomographic image, resulting in deterioration of diagnostic reliability.

In view of the above, in the present embodiment, characteristics of respiration are calculated based on the detection result obtained by CT imaging, without using a dedicated respiratory sensor. The procedures of calculating body motion characteristics will be described below.

As described above, in CT imaging, projection data 80 as shown in FIG. 3 is collected at prescribed rotational angles. The body motion characteristic calculation section 46 extracts fluctuations of data due to respiratory motion from the projection data collected at each prescribed rotational angle, and calculates a cycle of respiratory motion based on the extracted result. The fluctuations of data resulting from the respiratory motion can be extracted using the process described below, for example.

As shown in FIG. 3, the X-ray detector 60 is provided with a plurality of X-ray detection elements 61_1, 61_2, ... and 61_N, and an X-ray intensity is detected for each of the X-ray detection elements 61_1, 61_2, ... and 61_N. Projection data is data in which the X-ray intensity is converted into an X-ray attenuation value. As such, it is assumed that projection data of one time includes N sets of X-ray attenuation values, N being the number of the X-ray detection elements.

Figure 6A:
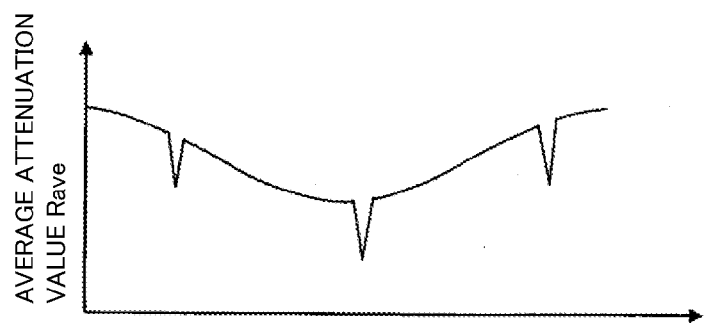
FIG. 6a is a graph showing an average value Rave of the calculated X-ray attenuation values.

When extracting data fluctuations caused by the respiratory motion, the body motion characteristics calculation section 46 calculates an average value Rave of the N sets of X-ray attenuation values at each prescribed rotational angle. FIG. 6a is a graph showing the calculated average Rave of the X-ray attenuation values. In FIG. 6a, the horizontal axis indicates a detection time, and the vertical axis indicates an X-ray attenuation value average value Rave.

As shown in FIG. 6a, the average value Rave of the X-ray attenuation values generally fluctuate in a near sine-wave, while experiencing periodic downward spikes. The fluctuations in a near sine-wave are caused by rotation of the measurement unit (X-ray generator 60 and the X-ray detector). The downward spikes, generated periodically, are caused by respiratory motion. As such, by extracting the downward spikes, it is possible to extract data fluctuations caused by respiratory motion. However, when data fluctuations caused by rotation of the measurement unit also exist along with the respiratory spikes, extracting only the data fluctuations caused by the respiratory motion is extremely difficult.

As such, the body motion characteristic calculation section 46 eliminates or reduces data fluctuations cause by rotation of the measurement unit from an approximate value of the average value Rave of the X-ray attenuation values. Specifically, the body motion characteristic calculation section 46 calculates an approximate curve of the attenuation value average value Rave, and calculates the difference between the approximate curve and the attenuation value average value Rave. It should be noted that the approximate curve may be calculated using a well-known conventional art, such as median approximation and a moving-average method.

Figure 6B:
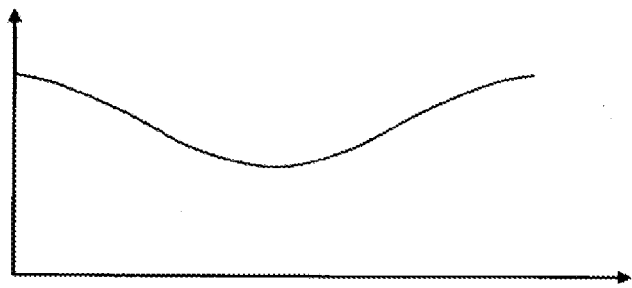
FIG. 6b is a graph showing an exemplary approximation curve of the average value Rave.
Figure 6C:
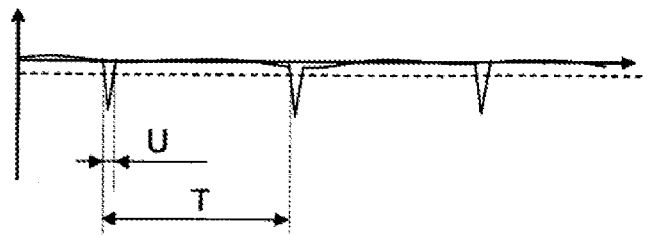
FIG. 6c is a graph showing a difference value between the average value Rave and the approximate curve.

FIG. 6b shows an example of a calculated approximate curve, and FIG. 6c shows a calculated difference value. As is obvious from FIG. 6c, by calculating a difference between the attenuation value average value Rave and the approximate curve, it is possible to obtain data in which data fluctuations due to the measurement unit, that is, fluctuations following a near sine curve, are significantly reduced.

With the obtained difference data, the body motion characteristic calculation section 46 calculates a generation cycle of downward spikes generated in the average value Rave of the X-ray attenuation value, a peak width, and the like, by binarizing the difference data with a predetermined threshold, for example. Then, the body motion characteristic calculation section 46 temporarily stores the obtained generation cycle of the spikes as a respiration cycle T and the peak width as a period of motion U, in the storage device 34.

As is clear from the above description, according to the present embodiment, respiratory motion cycles and the like can be obtained from projection data obtained through CT imaging. In other words, when the present invention is applied, there is no need to provide a dedicated sensor for detecting a cycle and the like of the respiratory motion. Consequently, the cost of a respiration sensor can be reduced, and the time and effort otherwise required for handling a respiration sensor can be eliminated. Further, deterioration of reliability in diagnosis caused by a respiration sensor being shown in a tomographic image can be eliminated. Furthermore, calculation of the body motion characteristics is performed based on data obtained through CT imaging which is indispensable for forming a tomographic image. In other words, according to the present embodiment, there is no need to perform extra X-ray irradiation for calculating body motion characteristics. As a result, an adverse effect of exposure to radiation and an increase in processing time can be prevented.

It should be noted that, although the body motion characteristics are calculated based on the average value Rave of the X-ray attenuation values, body motion characteristics may be calculated based on other parameters such as an integrated value of X-ray attenuation values, an integrated value or an average value of X-ray intensity, or the like, as long as the parameter indicates fluctuation tendency of the X-ray detection result. Body motion characteristics may also be calculated based on a location of the center of gravity M of the X-ray attenuation value R calculated by the following Expression 1. In Expression 1, $R_{CH}$ represents an X-ray attenuation value detected for an element number CH. Further, although an example involving respiratory motion has been used in the above description, the present invention may be applied to detection of characteristics of other cyclical body motions, including heartbeat motion.

[Equation 1]

$$M = \frac{\sum_{CH}(R_{CH} \times CH)}{\sum_{CH} R_{CH}} \quad (1)$$

Next, an example of respiration synchronized imaging performed in the present embodiment will be described. As described above, during CT imaging, when a subject position moves due to respiration, an artifact is generated in a tomographic image. In order to prevent this problem, it has been proposed to synchronize CT imaging and respiratory motion so as to perform CT image capturing when the subject is most at rest. This technique is effective if the time required for one CT imaging, that is, the time required for rotating the measurement unit 180 degrees, is sufficiently shorter than the rest period of the subject. However, to enable CT imaging at such a high speed, it is necessary to provide a high-performance, high-cost driving mechanism or the like, which in turn increases the cost of the X-ray CT scanner. Beyond this problem, there is an unsolved problem that this technique cannot be adopted at all when the time required for one CT imaging is longer than the rest period of the subject.

In order to solve this problem, in the present embodiment, CT imaging is performed a plurality of times for one imaging site by shifting the phase of body motion. Then, based on the data obtained by the CT imaging performed a plurality of times, a tomographic image is generated in which influences of the body motion are eliminated or reduced. More specifically, tomographic image is acquired using a process such as that described below. In the following, an example in which a period of motion is smaller than T/2, where T indicates a respiration cycle, will be described for ease of understanding.

Figure 7:
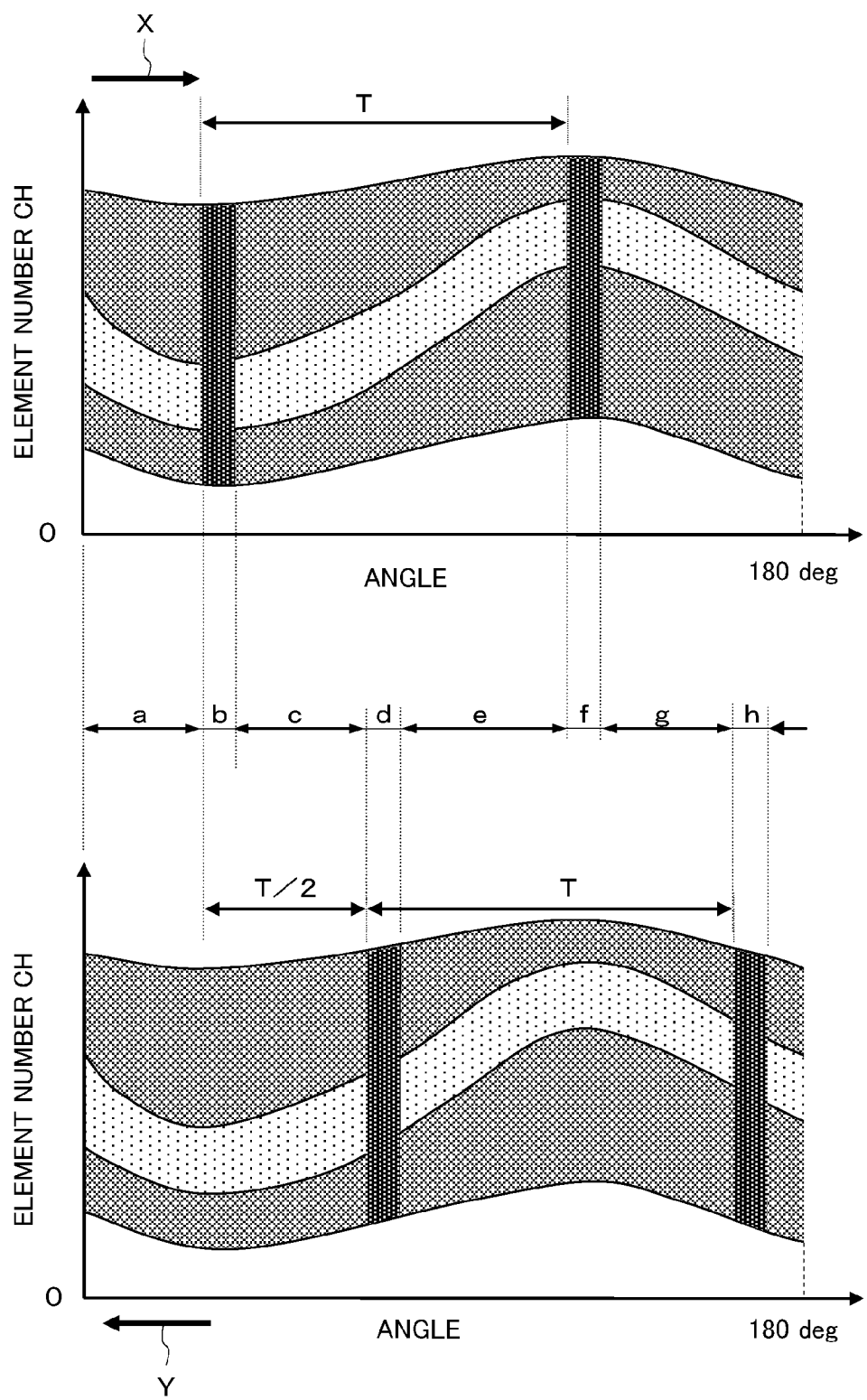
FIG. 7 shows exemplary images of sinograms obtained as a result of CT imaging.

To generate a tomographic image, the operation control section 44 drives the rotating mechanism 66, the measurement unit, and the like to perform first CT imaging. In order to do so, irradiation and detection of an X-ray are performed while rotating the measurement unit relative to the subject. When the first CT imaging has been performed, the body motion characteristics calculation section 46 calculates a respiration cycle T and a period of motion U based on the projection data obtained by the CT imaging. Further, the sinogram generation section 47 generates a first sinogram while arranging the projection data obtained from this imaging in the order of the rotational angles. The upper part of FIG. 7 shows an image of the first sinogram 70a obtained by the first CT imaging.

When the first CT imaging has been completed, the operation control section 44 then performs the second CT imaging by driving the rotating mechanism 66, and the measurement unit, and the like. For the second CT imaging, the start time is controlled based on the body motion characteristics calculated from the result of the first CT imaging. Specifically, for the second CT imaging, the time is controlled such that the respiration phase relative to the rotation of the measurement unit is inversed with respect to that of the first CT imaging. This means that the time to perform the second CT imaging is controlled such that the respiration time is shifted by a half cycle (T/2) from that in the first sinogram 70a in the second sinogram 70b generated from projection data obtained by the second CT imaging, as shown in the lower part of FIG. 7.

It should be noted that in the present embodiment, the rotating direction of the measurement unit is reversed for each CT imaging. As such, if the measurement unit is rotated in a clockwise direction from 0 degree to 180 degrees in the first CT imaging, the measurement unit is rotated in a counterclockwise direction from 180 degrees to 0 degree in the second CT imaging. The time flow in the first sinogram 70a in such a case is as shown by an arrow X in FIG. 7, and a direction that the rotational angle increases and a time elapsing direction are the same. On the other hand, in the second CT imaging operation, the rotational angle decreases as the detection time elapses. As such, the elapsing direction of the detection time in the second sinogram 70b, in which sets of data are arranged in the order of the rotational angles, is opposite to the direction that the rotational angle increases, as shown by an arrow Y. When performing the second CT imaging, it is necessary to control timing while considering the relationship between the elapsed time and the rotational angle. This will be described using FIG. 8.

Figure 8:
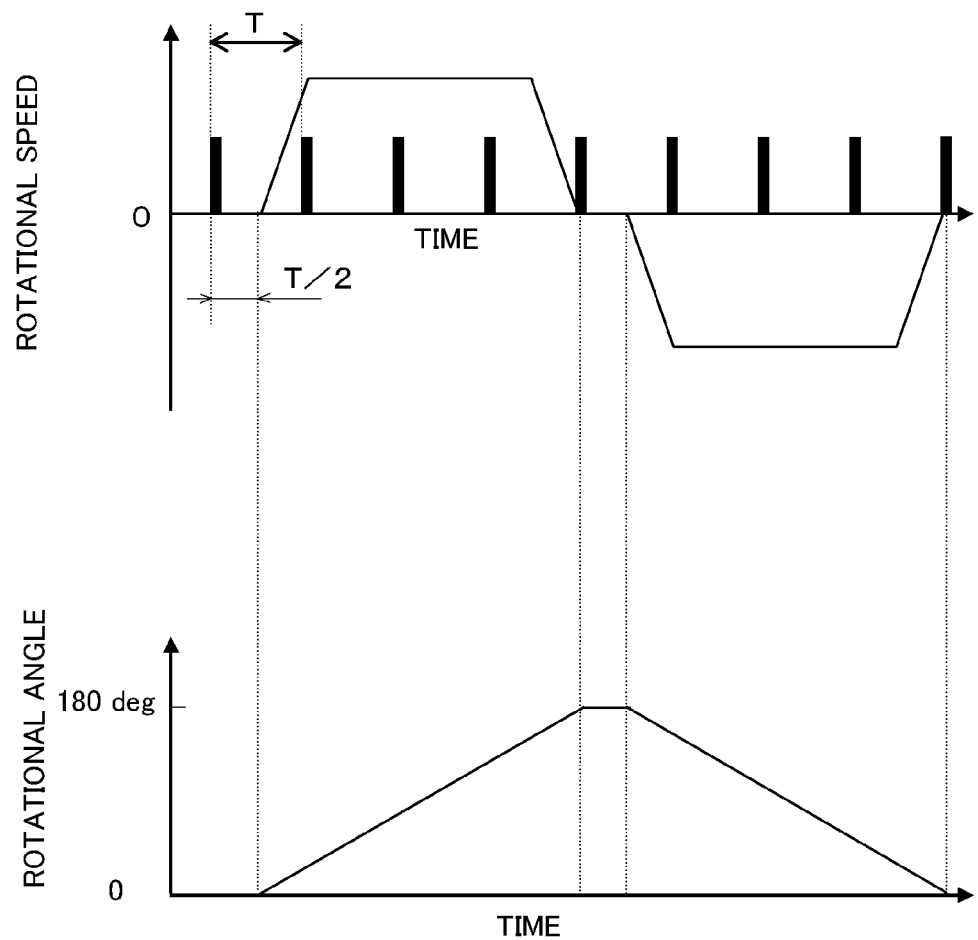
FIG. 8 is a graph showing a rotational speed and a rotational angle of a measurement unit when CT imaging is performed.

In FIG. 8, the upper graph shows a rotational speed of the measurement unit, and the lower graph shows a rotational angle of the measurement unit. Further, in FIG. 8, a bold vertical line shows the respiration timing. As shown in FIG. 8, it is assumed that the first CT measurement is started after T/2 has elapsed from the respiration start time. As such, it is necessary to drive-control the second CT measurement such that the end time thereof, that is, a time that the rotational angle reaches 0, becomes a respiration start time.

Figure 9:
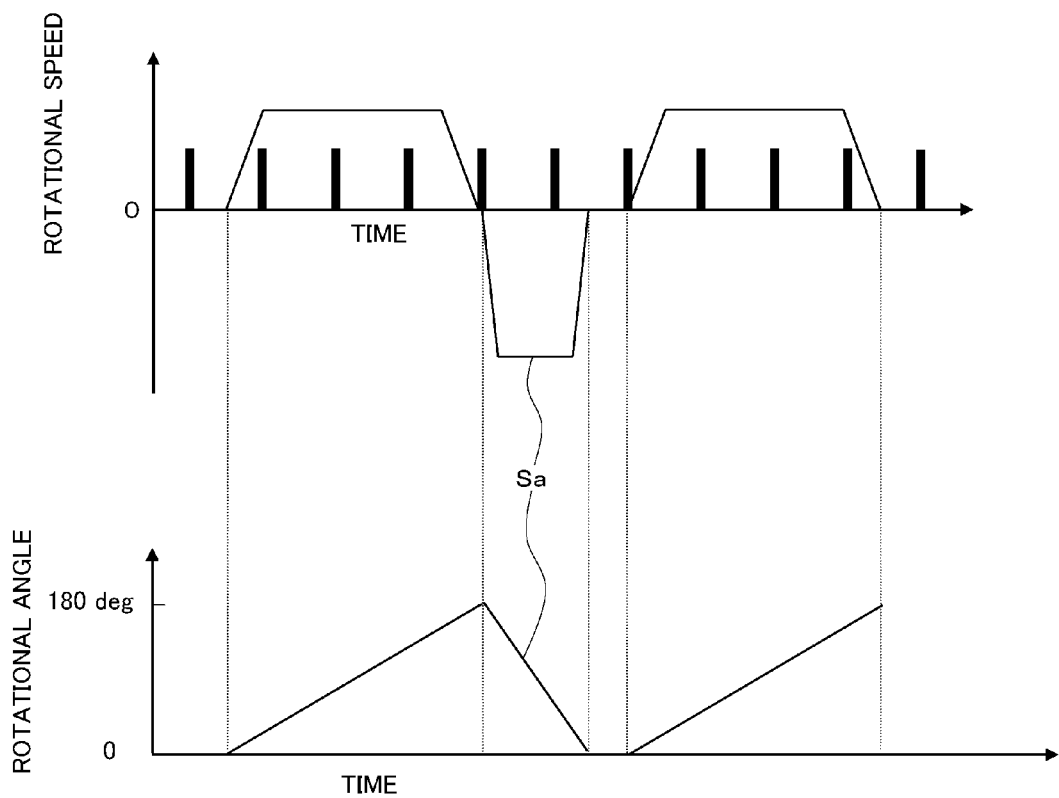
FIG. 9 is a graph showing another example of a rotational speed and a rotational angle of the measurement unit when CT imaging is performed.

It should be noted that, although in the present embodiment the rotational angle of the measurement unit is reversed for each CT image, it is also possible to add a step Sa at which the measurement unit returns to the initial position each time CT imaging is performed so that rotational directions of CT imaging are always the same, as shown in FIG. 9.

Using the sinograms 70a and 70b obtained by capturing two CT images, the sinogram correction section 48 generates a corrected sinogram in which data fluctuations due to respiratory motion is eliminated or reduced. Methods of generating the corrected sinogram include a method in which data in a period of motion of one sinogram, of two sinograms 70a and 70b, is compensated for using data of the other sinogram. This method will be described referring to FIG. 7. Data in sections "b" and "f" corresponding to the period of motions in the first sinogram 70a may be replaced with data in sections "b" and "f" of the second sinogram, which becomes a corrected sinogram. It should be noted that it is desirable to obtain an average between the two sinograms 70a and 70b for the sections where the subject rests for either the first or second CT imaging. That is, in FIG. 7, for each of the sections "a", "c", "e", and "g", it is desirable to use an average value between the first sinogram 70a and the second sinogram 70b. By using an average value as described above, influences of noise can be reduced, making it possible to obtain a more preferable, clearer, and more useful tomographic image.

Figure 10A:
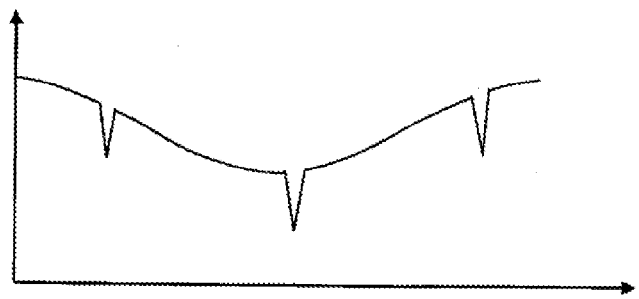
FIG. 10a is a graph showing an average value $Rave_1$ of the X-ray attenuation values obtained from the first CT imaging.
Figure 10B:
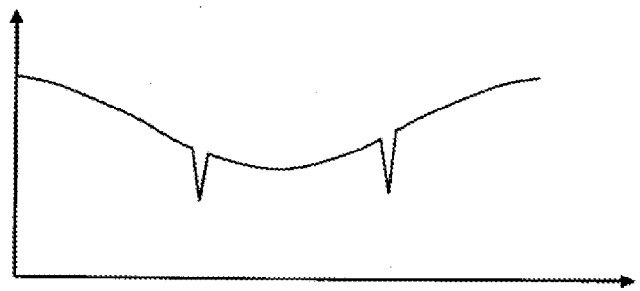
FIG. 10b is a graph showing an average value $Rave_2$ of the X-ray attenuation values obtained from the second CT imaging.
Figure 10C:
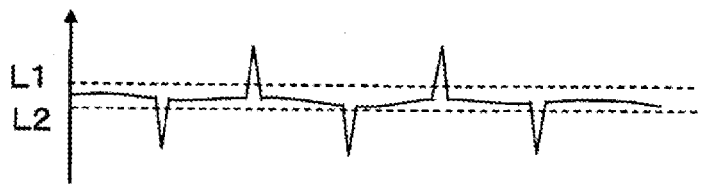
FIG. 10c is a graph showing a difference value between the two average values $Rave_1$ and $Rave_2$ of the X-ray attenuation values.

It should be noted that, although the periods of motion (sections "b", "d", and "f") in each of the sinograms 70a and 70b maybe calculated from the body motion characteristics calculated by the body motion characteristic calculation section 46, it is desirable to calculate the periods of motion from projection data obtained from the first and second CT imaging. Specifically, an X-ray attenuation value average value $Rave_1$ in the first CT imaging (see FIG. 10a) and an X-ray attenuation value average value $Rave_2$ in the second CT imaging (see FIG. 10b) are respectively calculated. Then, a difference between those two X-ray attenuation value average values is calculated. For the first CT imaging and the second CT imaging, the conditions other than the respiratory phases are the same, which means conditions such as the imaging sites and the intensity of irradiated X-rays are the same. As such, the difference value between the X-ray attenuation value average values should be data in which only the data fluctuations due to respiration remain, as shown in FIG. 10c and the processor 30 must only specify the periods of motion (sections "b", "d", and "f") by comparing the obtained difference data and the predefined thresholds L1 and L2, for example. As described above, by specifying the periods of motion from projection data obtained from the first and the second CT imaging, the periods of motion can be specified accurately, even if the respiration cycles and moving times differ between the first and second CT imaging operations.

As another method of generating a corrected sinogram, it is also possible to calculate average data of the first sinogram 70a and the second sinogram 70b as a corrected sinogram. With this method, data fluctuations due to respiratory motion cannot be eliminated completely, but can be reduced by half. Consequently, influences of respiratory motion can be reduced, and a tomographic image superior to that which can be obtained with a conventional art can be acquired.

After the corrected sinogram has been generated, the tomographic image generation section 49 generates a tomographic image based on the corrected sinogram. Because data fluctuations due to respiration have been eliminated or reduced in this corrected sinogram, a superior tomographic image including less motion artifacts can be acquired based on the corrected sinogram.

Figure 11:
FIG. 11 shows a tomographic image of the present embodiment calculated from a corrected sinogram.
Figure 12:
FIG. 12 shows a conventional tomographic image calculated from an uncorrected sinogram.

FIG. 11 shows a tomographic image generated based on the corrected sinogram. Further, FIG. 12 shows a tomographic image generated based on the uncorrected sinogram. As is obvious from a comparison between FIGS. 11 and 12, motion artifacts are significantly reduced in the tomographic image generated based on the corrected sinogram compared with the tomographic image based on the uncorrected sinogram. From the corrected image, a user can perceive a state of each site described in the tomographic image more precisely, and can therefore more likely make an accurate diagnosis.

When CT imaging has been performed on one imaging site a required number of times to generate a tomographic image, the operation control section 44 drives the sliding mechanism to move the subject in a rotational axis direction. Then, respiration synchronized imaging is performed on the new imaging site in the same manner as described above. This means that the first CT imaging is performed, and, based on the obtained projection data, body motion characteristics are calculated, that is, a sinogram is generated. Then, the second CT imaging is performed using time control based on the calculated body motion characteristics, whereby a second sinogram is generated. As such, according to the present embodiment, new body motion characteristics are calculated each time the imaging site is updated. As a result, even if body motion characteristics such as a respiratory cycle change over time, the change can be followed.

As is obvious from the above description, in the present embodiment, as influences of body motion are reduced in a soft manner, highly reliable diagnosis can be performed. It should be noted that, although the relationship between the period of motion U and the respiration cycle T is assumed to be U<T/2 in the above example, the present embodiment can also be applied to cases were U≥T/2. When U≥T/2, it is only necessary to perform CT imaging at least three times while shifting the respiratory phases, and then, based on the three or more sinograms, generate a corrected sinogram in which data fluctuations due to respiration are eliminated or reduced. When performing the third CT imaging, body motion characteristics are recalculated based on projection data obtained during the second CT imaging, and the start time of the third CT imaging is controlled based on the recalculated body motion characteristics. This is also the same for the fourth and subsequent CT imaging; body motion characteristics are recalculated based on projection data obtained by the $N^{th}$ CT imaging, and the start time of the $N+1^{th}$ CT imaging is controlled based on the recalculated body motion characteristics. In other words, the start time of the second CT imaging or after is controlled based on the body motion characteristics calculated based on projection data obtained by the immediately preceding CT imaging. Thereby, an accurate respiratory cycle and the like can always be obtained, even if the respiratory cycle or the like changes over time.

REFERENCE NUMERALS 10 measurement section, 12 computation control section, 16 main body, 18 gantry, 20 operation panel, 24 container, 26 arm, 30 processor, 32 display, 34 storage device, 36 keyboard, 38 mouse, 40 printer, 42 communication section, 44 operation control section, 46 body motion characteristic calculation section, 47 sinogram generation section, 48 sinogram correction section, 49 tomographic image generation section, 52 X-ray generator, 54 collimator, 56 X-ray beam, 58 effective field of view, 60 X-ray detector, 61 X-ray detection element, 62 displacement mechanism, 66 gantry rotating mechanism, 68 sliding mechanism, 70 sinogram, 100 subject.

The invention claimed is:

1. An X-ray CT scanner comprising:
an X-ray generator;
an X-ray detector which is arranged opposite to the X-ray generator across a subject and which is formed with a plurality of X-ray detecting elements;
a measurement section that performs CT imaging at least twice by irradiating X-rays while relatively rotating the X-ray generator and the X-ray detector 180 degrees with respect to the subject over a time longer than a respiratory cycle of the subject, and collecting detection values detected by the plurality of X-ray detecting elements as detection result data at prescribed rotational angles;
a body motion characteristic calculation section that, in a first CT imaging, calculates, for each of the prescribed rotational angles, one of an average value, an integrated value, and a location of center of gravity of the detection values detected by the plurality of X-ray detecting elements obtained at the prescribed rotational angles, extracts a data fluctuation caused by respiration of the subject by eliminating or reducing a data fluctuation caused by rotation of the X-ray generator and the X-ray detector from data of a temporal change in one of the calculated average value, the integrated value, and the location of center of gravity of the detection values obtained at the prescribed rotational angles in the first CT imaging, and calculates a characteristic of the respiration of the subject based on the extracted values;
a drive control section that allows the measurement section to perform CT imaging on the same target site a plurality of times, the drive control section controlling execution of a second or subsequent CT imaging based on the characteristic of the respiration calculated by the body motion characteristic calculation section, such that phases of the respiration relative to rotational angles of the X-ray generator and the X-ray detector differ between the plurality of times of CT imaging; and
an image generation section that generates a tomographic image in which an influence of the respiration is eliminated or reduced, based on projection data obtained from the CT imaging performed on the same target site a plurality of times.

2. The X-ray CT scanner according to claim 1, wherein the image generation section includes:
a sinogram generation section that generates a sinogram by arranging sets of projection data obtained by the CT imaging in order of the rotational angles;
a sinogram correction section that generates a corrected sinogram in which data fluctuation caused by the respiration is reduced or eliminated, from a plurality of sinograms corresponding to the same imaging site; and
a tomographic image generation section that generates a tomographic image based on the corrected sinogram.

3. The X-ray CT scanner according to claim 2, wherein the sinogram correction section compensates for a portion of one sinogram containing a fluctuation caused by respiration using data of a corresponding angular portion in another sinogram of the same imaging target site.

4. The X-ray CT scanner according to claim 3, wherein for an angular portion where no data fluctuation is caused by respiration in all of the plurality of sinograms of the same imaging target site, the sinogram correction section calculates an average among the plurality of sinograms.

5. The X-ray CT scanner according to claim 1, wherein the body motion characteristic calculation section calculates a characteristic of the respiration based on detection result data obtained by the $N^{th}$ CT imaging among N+1 CT imaging operations performed on an imaging site, and
the drive control section determines a start time of the $(N+1)^{th}$ CT imaging based on the characteristic of the respiration calculated from the detection result data of the $N^{th}$ CT imaging.

6. The X-ray CT scanner according to claim 1, wherein the body motion characteristic calculation section recalculates a characteristic of the respiration each time an imaging target site is changed.

7. The X-ray CT scanner according to claim 1, wherein the measurement section causes the rotating direction of the X-ray generator and the X-ray detector to be reversed for each of the plurality of times of CT imaging.

8. A non-transitory computer-readable medium containing control program for an X-ray CT scanner, the program, when executed by a computer, allowing the computer, which is connected to a measurement device that performs CT imaging at least twice by irradiating an X-ray while relatively rotating an X-ray generator and an X-ray detector, which is arranged opposite to the X-ray generator across a subject and which is formed with a plurality of X-ray detecting, to function as:
a measurement section that performs CT imaging at least twice by irradiating X-rays while relatively rotating the X-ray generator and the X-ray detector 180 degrees with respect to the subject over a time longer than a respiratory cycle of the subject, and collecting detection values detected by the plurality of X-ray detecting elements as detection result data at prescribed rotational angles;
a body motion characteristic calculation section that, in a first CT imaging, calculates, for each prescribed rotational angle, one of an average value, an integrated value, and a location of center of gravity of the detection values detected by the plurality of X-ray detecting elements obtained at each prescribed rotational angle, extracts a data fluctuation caused by respiration of the subject by eliminating or reducing a data fluctuation caused by rotation of the X-ray generator and the X-ray detector from data of a temporal change in one of the calculated average value, the integrated value, and the location of center of gravity of the detection values obtained at the prescribed rotational angles in the first CT imaging, and calculates a characteristic of the respiration of the subject based on the extracted result;
a drive control section that allows the measurement section to perform CT imaging on the same target site a plurality of times, the drive control section controlling execution of second CT imaging or after based on the characteristic of the respiration calculated by the body motion characteristic calculation section such that phases of the respiration relative to rotational angles of the X-ray generator and the X-ray detector differ between the plurality of times of CT imaging; and an image generation section that generates a tomographic image in which an influence of the respiration is eliminated or reduced, based on projection data obtained from the CT imaging performed on the same target site a plurality of times.

* * * * *